United States Patent [19]

Zimmon

[11] Patent Number: 5,052,998
[45] Date of Patent: Oct. 1, 1991

[54] INDWELLING STENT AND METHOD OF USE

[76] Inventor: David S. Zimmon, 7 Farm View Rd., Port Washington, N.Y. 11050

[21] Appl. No.: 504,575

[22] Filed: Apr. 4, 1990

[51] Int. Cl.$^5$ .............................................. A61M 5/00
[52] U.S. Cl. ...................................... 604/8; 604/281; 604/54
[58] Field of Search ................................ 604/280-283, 604/269, 8, 164, 170, 175, 9-10, 54, 55, 93

[56] References Cited

U.S. PATENT DOCUMENTS

| | | | |
|---|---|---|---|
| 3,938,529 | 2/1976 | Gibbons | 604/8 |
| 4,230,123 | 10/1970 | Hawkins, Jr. | 120/753 |
| 4,382,445 | 5/1983 | Sommers | 604/8 |
| 4,462,402 | 7/1984 | Burgio et al. | 128/DIG. 26 |
| 4,531,933 | 7/1985 | Norton et al. | 604/281 |
| 4,643,716 | 2/1987 | Draeh | 604/281 |
| 4,699,611 | 10/1987 | Bowden | 604/105 |
| 4,887,996 | 12/1989 | Bergmark | 604/281 |
| 4,950,228 | 8/1990 | Krapp, Jr. et al. | 604/281 |
| 4,957,479 | 9/1990 | Roemer | 604/281 |

OTHER PUBLICATIONS

Wilson-Cook Medical Inc. catalog, ©1988, pp. 19, 21-23.

Primary Examiner—John D. Yasko
Assistant Examiner—Kathleen A. Doley
Attorney, Agent, or Firm—Woodard, Emhardt, Naughton, Moriarty & McNett

[57] ABSTRACT

A stent 21 is disclosed having a pigtail 33 at its distal end 35 and having a flap 23 acting as a barb at its proximal end 29. Stent 21 includes a catheter body 31 having at least one lumen 43 and having drainage holes 37, 39. The stent may be made of radiopaque polyethylene. The pigtail 33 prevents proximal migration of catheter body 31 while allowing spring action to accommodate variations in length, while flap 23 prevents entire distal migration while being radially retractable to facilitate insertion. An alternative embodiment is disclosed having multiple flaps 25, 27 acting as a barb. A method of use is also disclosed.

17 Claims, 3 Drawing Sheets

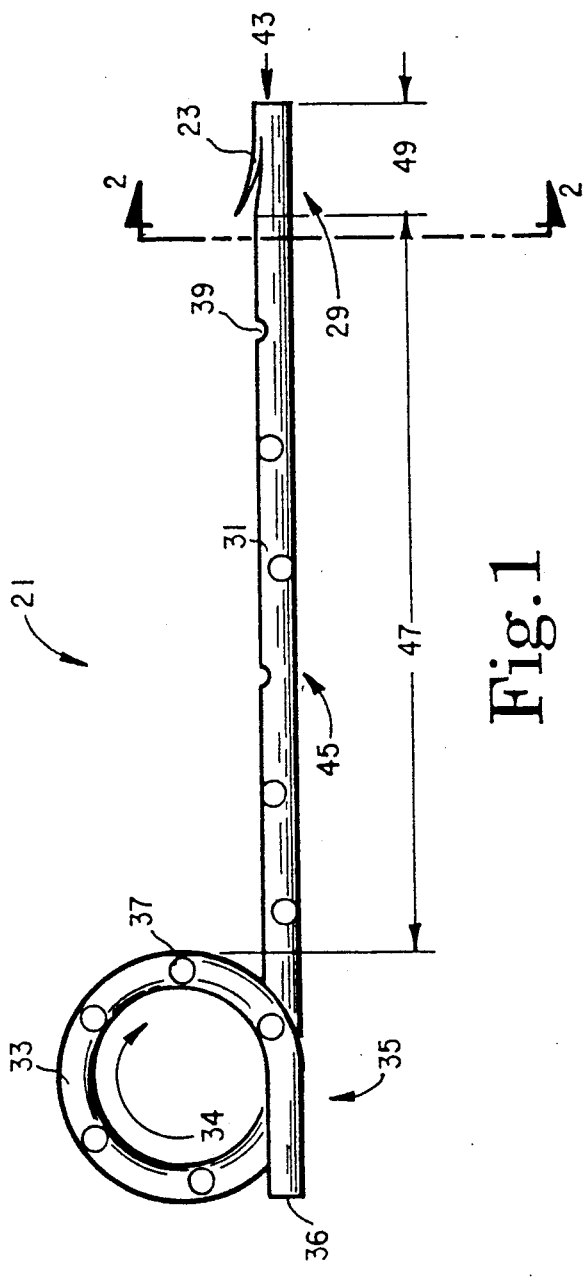
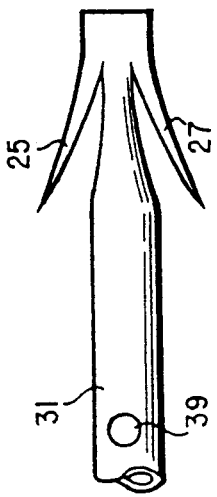

INDWELLING STENT AND METHOD OF USE

BACKGROUND OF THE INVENTION

A stent is a mechanical device used to dilate and/or maintain a desired lumen in a tubular structure or duct as in the bile duct, pancreatic duct, cystic duct, ureter or urethra. Stones, contracting scar tissue or compressing neoplasia, benign or malignant, may compromise a duct lumen and are the indications for stent placement. The stent must be rigid to be forced through and dilate a narrowed area (stenosis) but sufficiently pliable to conform to the adjacent normal tissue without injuring it by erosion. Furthermore, a method must be provided to maintain the stent in place without proximal and distal migration. A stent may pass distally out of position within the duct or be lost proximally toward or into the organ. In either case, the result is failure to maintain a patent lumen and return of the obstruction and its symptoms. A passed stent must be replaced. A lost stent must be retrieved from within the organ, manipulated through the narrowing (stenosis), removed and then replaced. Beyond the technical complexity of retrieving a lost stent, the obstruction and its consequences must first be treated. These considerations emphasize the need to prevent stent loss in preference to the more easily replaced stent that has passed.

Initially, stents with pigtails on both ends (double pigtails) were used in the biliary tree including the bile and cystic ducts and the pancreas as well as the urinary tract. As technical skill and endoscopes improved, it became possible to use larger diameter stents greater than the initial 5 French (1.7 mm O.D., 1 mm I.D.). With increased stent diameter and rigidity, the pigtail exerted greater force on the wire guide used for introduction, and it became more difficult to force the stent over the wire guide through a tight stenosis without buckling. Consequently, the pigtail was replaced with a flap, particularly in stents of 10 French diameter and greater. This strategy improved introduction at the expense of the more efficient retention of a pigtail. A small flap on both ends of the stent and long stents of 12 to 15 cm used in the biliary tree prevented this displacement by both resistance of the flap to movement and length of the stent.

However, the double flap or wing stent also has disadvantages. It is difficult to select the proper length as after stent placement, and after relief of obstruction there is substantial shrinkage of the duct system that may make a straight flap stent too long and erode or gouge tissue causing pain or bleeding with premature stent obstruction. Flap stents may easily be lost into the obstructing duct during the last few forceful pushes during introduction. The relatively small wings may fracture and break off during introduction or break off due to loss of elasticity. Large 10 or 11.5 French stents are rigid and difficult to grasp for removal. This is particularly true if the stent is lost into the proximal duct system or organ cavity. The larger flaps of a 10 French or larger stent gouge or scrape the tissue on removal. This may provoke bleeding that leads to immediate occlusion of the replacement stent. These problems with flap stents are exaggerated in the pancreas where 5 and 7 French (1.7 and 2.1 mm O.D.) stents 3 to 5 cm in length are required and there is a relatively long duct (10 to 12 cm in length are required and there is a relatively long duct (10 to 12 cm) into which the stent may be lost.

SUMMARY OF THE INVENTION

According to one embodiment, the present invention provides an indwelling stent, comprising: a catheter body having a tube wall surrounding a lumen and having drainage to allow fluids to pass in and out of said lumen. The catheter body has a distal end, a proximal end, and a central portion therebetween for maintaining a tubular structure in a patient open, and has a pigtail anchor means formed by a curl in the catheter body at the distal end for preventing entire proximal migration of the catheter body while allowing spring action in the curl to accommodate variations in length of the tubular structure in the patient. The proximal end has barb anchor means radially projecting from the proximal end for preventing entire distal migration of the catheter body, wherein the proximal end of the catheter body is substantially straight and wherein the barb anchor means are radially retractable toward the proximal end to facilitate insertion of the proximal end through the tubular structure in the patient.

A method of use of this stent is also provided.

One object of the present invention is to provide an improved stent and method of its use. These and other objects are set forth in the written description and drawings.

BRIEF DESCRIPTION OF THE DRAWINGS

FIG. 1 is a side elevational view of a first embodiment of a stent according to the present invention, having one flap.

FIG. 2 is a cross-sectional view of the stent of FIG. 1 taken along line 2—2 of FIG. 1.

FIG. 3 is a partial side elevational view of a proximal end of an alternative embodiment of the present invention, having two flaps.

DESCRIPTION OF THE PREFERRED EMBODIMENT

Figure 4A:
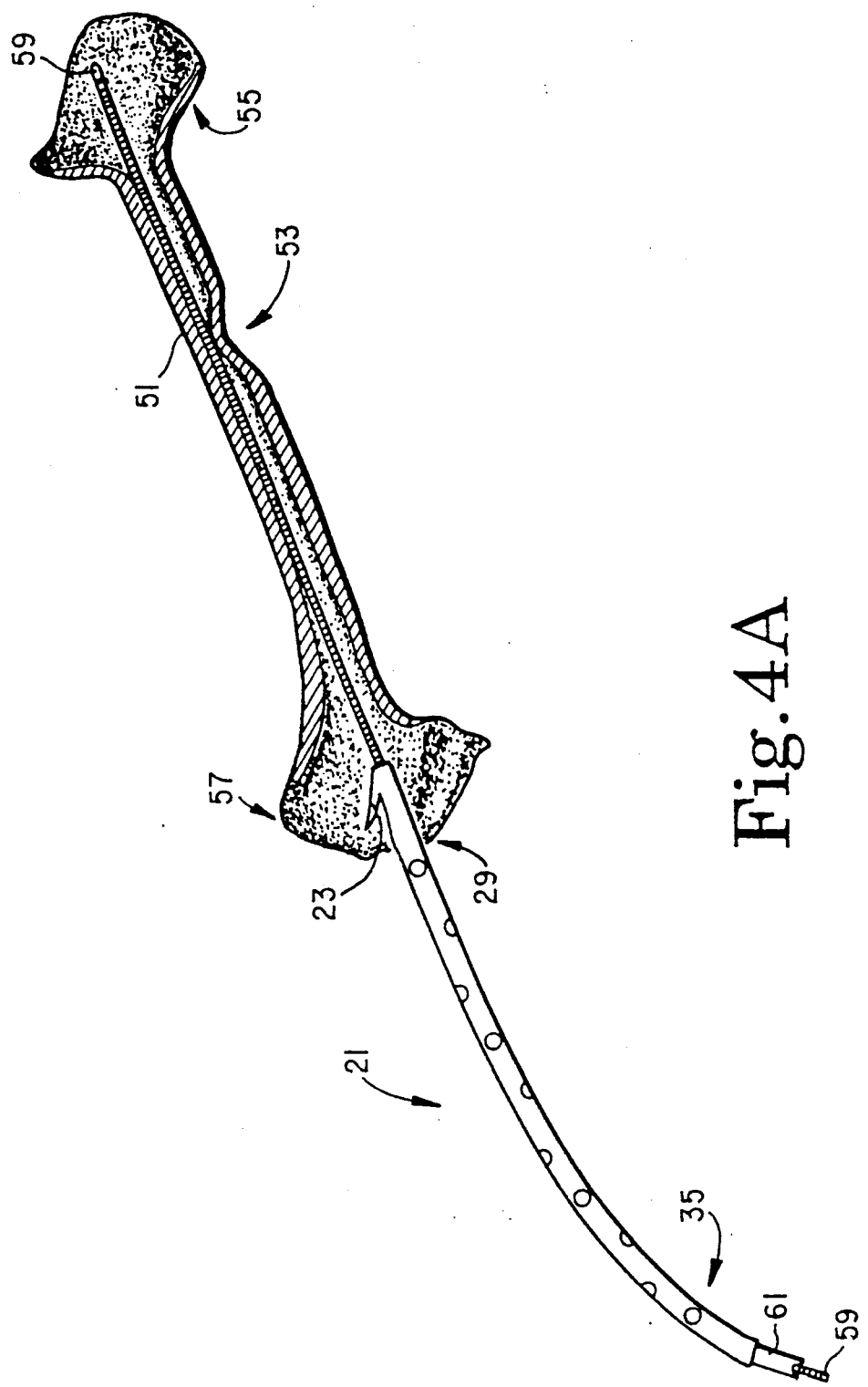
FIGS. 4A, 4B and 4C sequentially illustrate a method of using the stent of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device and method, and such further applications of the principles of the invention as illustrated therein being contemplated as would normally occur to one skilled in the art to which the invention relates.

The previously described problems are resolved by this invention, stent 21, that combines a proximal modified flap 23 at proximal end 29 of catheter body 31, or flaps 25 and 27 (see FIG. 3) along with a modified distal pigtail 33 at distal end 35. The single large flap 23 may be replaced with multiple smaller flaps 25 and 27 as shown in the alternative embodiment of FIG. 3. Two or more such flaps may be used. A distal flap is replaced with pigtail 33 that contains multiple side holes, such as hole 37 for drainage, to reduce reflux and provide a spring-like retention device. The small flaps 25 and 27 are soft and not traumatic to adjacent tissues and can be removed without gouging or scraping.

Catheter body 31 has tube wall 41 surrounding at least one lumen, such as lumen 43 (see FIG. 2). Inbetween distal end 35 and proximal end 29 of catheter body 31 central portion 45 of the catheter body is located having a length 47. Typically, length 47 is between 2 cm and 12 cm. Preferably, catheter body 31 is made of polyethylene which is radiopaque.

Referring to FIG. 2, preferably the present invention has catheter body 31's dimensions such that it has an outside diameter of at least 1.7 mm and tube wall 41 has a thickness of at least 0.35 mm. Other sizes may be provided and it is contemplated that French sizes 5 and 7 (among others) may be used. Flap 23 has a flap length 49 which in the preferred embodiment is 7 mm. Distal end 35 includes distal tip 36. Note that in the preferred embodiment, pigtail 33 has a curl 34 which is 360° with distal tip 36 parallel with central portion 45 of the catheter body. It is to be understood that for purposes of this application, a pigtail anchor can include pigtails having curvatures lessor or greater than 360°, and may have multiple curls. Proximal end 29 preferably is made with a flap 23 as illustrated which preferably is formed by a generally longitudinal cut in tube wall 41. Typically due to the cylindrical shape, this longitudinal cut generally takes a "U" or "V" shape and provides a drainage opening in addition to holes which may be provided such as hole 39. Flap 23, as well as flaps 25 and 27, act as a barb mechanism allowing easy insertion through tubular structure 51 in a patient. (See FIGS. 4A–4C). A variety of structures may provide this barb action with the barb radially projecting from proximal end 29 for preventing entire distal migration of catheter body 31 while having the barb radially retractable towards proximal end 29 so catheter body 31 is substantially straight to facilitate insertion of the proximal end in tubular structure 51.

Figure 4B:
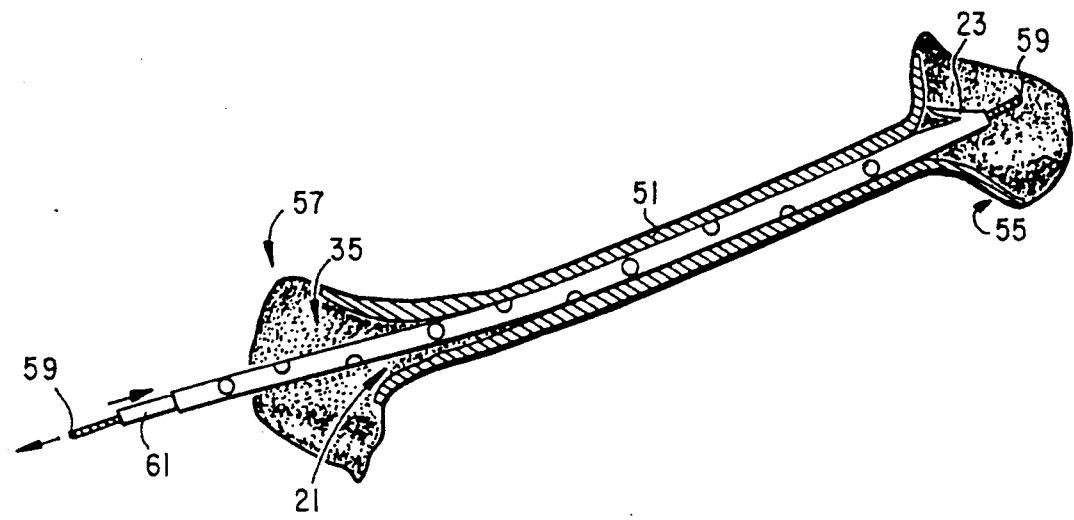
Figure 4C:
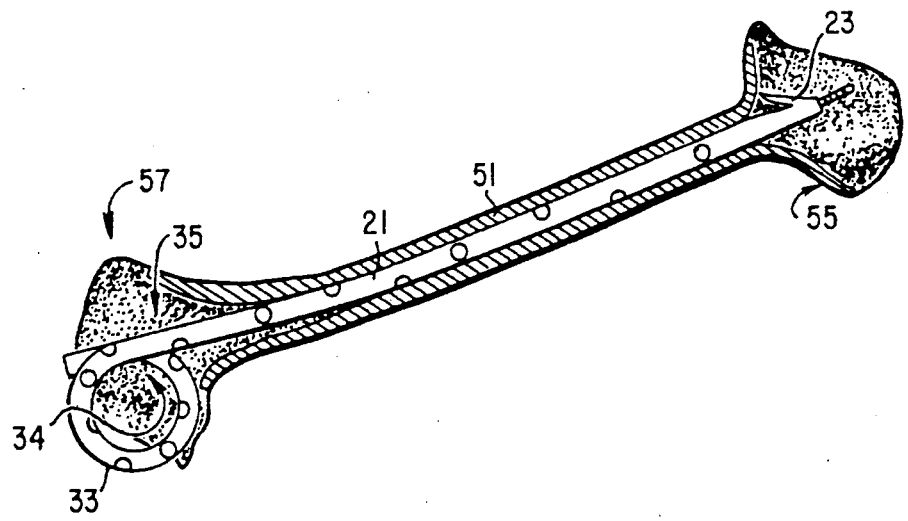

A method of using the present invention is illustrated in FIGS. 4A, 4B and 4C. Preferably, wire guide 59 is inserted in lumen 43 of stent 21, straightening out curl 34 (see FIG. 4A). Wire guide 59 is inserted through tubular structure 51 in the patient past stenosis 53.

Referring to FIGS. 4A and 4B, stent 21 is advanced along wire guide 59, preferably by a pushing action from positioner 61 (partially shown) located around wire guide 59. When the barb anchor, such as flap 23, is in a position (see FIG. 4B and FIG. 4C) proximally beyond tubular structure 51, typically in proximal organ 55, then wire guide 59 is withdrawn from lumen 43 of the stent wherein curl 34 is reformed (see FIG. 4C). Pigtail 33's curl 34 acts to prevent proximal migration away from distal organ 57. It is to be understood that typically this method is to be performed endoscopically.

To facilitate stent removal and exchange the distal 5 to 10 mm of the large 10 French or greater stents is drawn to a 5 French diameter or to a string-like extension that permits removal with a small diameter (5 to 7 French) more maneuverable grasping forceps and prevents stent loss proximally. This invention combines the ease of introduction provided by a straight proximal stent end that tapers to closely fit the introduction wire guide 59 without distortion and the spring-like distal pigtail 33 to prevent stent 21 loss during or after introduction and allow removal with a smaller more maneuverable grasping forceps. The multiple side holes of the distal pigtail 33 prevent free reflux of intestinal or urinary contents into the proximal duct system while maintaining decompression and drainage. The multiple smaller flaps reduce gouging and bleeding on stent removal and exchange. The spring-like effect of the distal pigtail 33 obviates the need for long stents to maintain duct position. This allows the use of short more efficient stents for distal duct stenosis and removes the risk of tissue injury from the distal stent end 35 as well as the mechanical problem of forceful introduction of long large bore (greater than 10 French) stiff stents that must be bent to pass in a tight U-turn from endoscope into the duct. Taken together, these changes significantly improve the ease of introduction and removal as well as the efficiency of residence of these devices. The effect of these inventions will reduce the frequency of stent change and increase efficiency by reducing the number of procedures that patients are required to undergo during treatment with stents.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An indwelling stent, comprising:
  a catheter body having a tube wall surrounding at least one lumen, said catheter body having drainage means for allowing fluids to pass in and out of said lumen, said catheter body further having a distal end for placement in a body cavity away from another body cavity to be drained, a proximal end for placement in the body cavity to be drained, and a central portion therebetween for maintaining a tubular structure in a patient open;
  pigtail anchor means formed by a curl in said catheter body at said distal end for preventing entire proximal migration of said catheter body while allowing spring action in said curl to accommodate variations in length of the tubular structure in the patient; and
  barb anchor means radially projecting from said proximal end for preventing entire distal migration of said catheter body out of the body cavity to be drained, wherein said proximal end of said catheter body is substantially straight and wherein said barb anchor means are radially retractable toward said proximal end to facilitate insertion of said proximal end through the tubular structure in the patient without passing said pigtail anchor means through the tubular structure in the patient.

2. The stent of claim 1 wherein said tube wall is relatively stiff and resists bending by having an outside diameter of at least 1.7 millimeters and further having a tube wall thickness of at least 0.35 millimeters.

3. The stent of claim 2 wherein said tube wall is formed of polyethylene.

4. The stent of claim 3 wherein said barb anchor means comprise at least one flap formed by a generally longitudinal cut in said tube wall.

5. The stent of claim 4 wherein said drainage means comprise a plurality of holes in said tube wall.

6. The stent of claim 5 wherein said central portion of said catheter body has a length between about two centimeters and twelve centimeters.

7. The stent of claim 6 wherein said curl is 360° with a distal tip of said pigtail anchor means parallel with said central portion of said catheter body.

8. The stent of claim 7 wherein said barb anchor means comprise a plurality of flaps formed by generally longitudinal cuts in said tube wall.

9. The stent of claim 1 wherein said tube wall is formed of polyethylene.

10. The stent of claim 1 wherein said barb anchor means comprise at least one flap formed by a generally longitudinal cut in said tube wall.

11. The stent of claim 1 wherein said drainage means comprise a plurality of holes in said tube wall.

12. The stent of claim 1 wherein said central portion of said catheter body has a length between about two centimeters and twelve centimeters.

13. The stent of claim 1 wherein said curl is 360° with a distal tip of said pigtail anchor means parallel with said central portion of said catheter body.

14. The stent of claim 1 wherein said barb anchor means comprise a plurality of flaps formed by generally longitudinal cuts in said tube wall.

15. A method of positioning an indwelling stent in a patient, comprising the steps of:

(a) providing a stent, comprising:

a catheter body having a tube wall surrounding at least one lumen, said catheter body having drainage means for allowing fluids to pass in and out of said lumen, said catheter body further having a distal end for placement in a body cavity away from another body cavity to be drained, a proximal end for placement in the body cavity to be drained, and a central portion therebetween for maintaining a tubular structure in a patient open;

pigtail anchor means formed by a curl in said catheter body at said distal end for preventing entire proximal migration of said catheter body while allowing spring action in said curl to accommodate variations in length of the tubular structure in the patient; and barb anchor means radially projecting from said proximal end for preventing entire distal migration of said catheter body out of the body cavity to be drained, wherein said proximal end of said catheter body is substantially straight and wherein said barb anchor means are radially retractable toward said proximal end to facilitate insertion of said proximal end through the tubular structure in the patient without passing said pigtail anchor means through the tubular structure in the patient;

(b) inserting a wire guide in said lumen, said wire guide straightening out said curl in said distal end and extending from said proximal end of said catheter body;

(c) inserting said wire guide through the tubular structure in the patient;

(d) advancing said stent along said wire guide and into the tubular structure to a position with said barb anchor means proximally beyond the tubular structure without passing said pigtail anchor means through the tubular structure; and (e) withdrawing said wire guide from said lumen wherein said curl is reformed distally with respect to the tubular structure in the patient.

16. The method of claim 15 wherein the tubular structure in the patient is a bile duct.

17. The method of claim 15 wherein the tubular structure in the patient is a pancreatic duct.

* * * * *

UNITED STATES PATENT AND TRADEMARK OFFICE
CERTIFICATE OF CORRECTION

PATENT NO. : 5,052,998

DATED : October 1, 1991

INVENTOR(S) : David S. Zimmon

It is certified that error appears in the above-identified patent and that said Letters Patent is hereby corrected as shown below:

On the Title page

Item 57 (the Abstract) at Line 6, please insert --entire-- after "prevents"

In Column 1 Lines 67 and 68, please delete "there is a relatively long duct (10 to 12 cm in length are required and"

Signed and Sealed this

Twenty-sixth Day of January, 1993

Attest:

STEPHEN G. KUNIN

*Attesting Officer*     Acting Commissioner of Patents and Trademarks